United States Patent [19]

Hartl et al.

[11] Patent Number: 5,776,724
[45] Date of Patent: Jul. 7, 1998

[54] CHAPERONIN-MEDIATED PROTEIN FOLDING

[75] Inventors: Franz-Ulrich Hartl, Unterschleissheim, Germany; Arthur L. Horwich, Westport, Conn.

[73] Assignee: Yale University, New Haven, Conn.

[21] Appl. No.: 451,066

[22] Filed: May 25, 1995

Related U.S. Application Data

[62] Division of Ser. No. 247,652, May 23, 1994, abandoned, which is a continuation of Ser. No. 721,974, Jun. 27, 1991, abandoned, which is a continuation-in-part of Ser. No. 673,158, Mar. 18, 1991, which is a continuation of Ser. No. 261,573, Oct. 24, 1988, abandoned.

[51] Int. Cl.[6] ............................................. C12P 21/00
[52] U.S. Cl. .................. 435/68.1; 435/69.1; 435/172.3; 530/300; 530/333; 530/350
[58] Field of Search ............................ 435/7.1, 68.1, 435/69.1, 172.3, 810; 530/300, 333, 350

[56] References Cited

PUBLICATIONS

Goloubinoff et al. (1989) Nature, vol. 342, pp. 884–888.
Lubben et al. (1990) Proc. Natl Acad. Sci (USA), vol. 87, No. 19, pp. 7683–7687.

*Primary Examiner*—Ardin H. Marshcel
*Attorney, Agent, or Firm*—Arnall Golden & Gregory, LLP

[57] ABSTRACT

The mechanisms and components required for chaperonin-dependent folding of proteins has been elucidated using the groEL and groES proteins of *E. coli* to reconstitute enzymatic activity of two monomeric enzymes, dihydrofolate reductase (DHFR) and rhodanese following dilution from denaturant. The essential elements for properly folding any protein are Mg-ATP (provided in the preferred embodiment as 5 mM Mg acetate and 1 mM ATP), groEL or hsp60, and groES or eukaryotic equivalent. These can be provided in purified form or as a semi-purified cell extract. The groES eukaryotic equivalent, encoded by a gene which does not hybridize to the groES gene, can be isolated using the same technique as was described to isolate Hsp60: isolation of a temperature sensitive lethal yeast mutant (petite at permissive temperature) defective in folding and assembly of imported proteolytically processed human ornithine transcarbamylase (OTC). The yeast mutant is used to identify a yeast genomic DNA sequence that rescues the mutant following library transformation. The rescuing DNA is isolated, characterized, and expressed. The expressed protein is used to make an antibody which is in turn used to identify the protein in yeast mitochondrial extracts and facilitate biochemical isolation of the protein.

9 Claims, 6 Drawing Sheets

CHAPERONIN-MEDIATED PROTEIN FOLDING

BACKGROUND OF THE INVENTION

This is a divisional of application U.S. Ser. No. 08/247,652 filed on May 23, 1994 by Franz-Ulrich Hartl and Arthur L. Horwich entitled "Method for Isolating Yeast DNA Encoding Proteins Involved in Chaperonin-Mediated Protein Folding," now abandoned, which is a continuation of U.S. Ser. No. 07/721,974 filed Jun. 27, 1991, now abandoned, which is a continuation-in-part of U.S. Ser. No. 07/673,158 entitled "Yeast Heat Shock Protein 60 and Analogs" filed Mar. 18, 1991 by Arthur L. Horwich, Mingyuan Cheng, Richard Hallberg, Donald S. Reading, and Alan Myers, which is a continuation of U.S. Ser. No. 07/261,573 filed Oct. 24, 1988, now abandoned.

Little is known about the mechanisms by which newly-synthesized proteins fold inside cells. Recent findings suggest that, for many proteins, folding in vivo may not be a spontaneous process. For example, while in vitro folding reactions are carried out on completed polypeptide chains, these studies fail to address the situation faced with proteins synthesized in intact cells. In the cell, the $NH_2$-terminal epitopes of a nascent protein, which are required for the protein folding, may already have emerged from a ribosome, before the remaining COOH-terminal portion of the protein has been synthesized. Similarly, the $NH_2$-terminal portion of a translocated polypeptide may emerge from the trans-side of a membrane before the COOH-terminal portion has translocated. In such instances, a "chaperoning" function is required to prevent illegitimate intra- and inter-molecular interactions of the nascent polypeptides.

A number of components have been identified which are involved in mediating protein folding in a variety of cell types and compartments, as reported by Fischer, G. & Schmid, F. X. *Biochemistry* 29, 2206–2212 (1990); Freedman, R. B. *Cell* 57, 1069–1072 (1989); and Ellis and van der Vinn, *Annu. Rev. Biochem.* 60:337–347 (1991). They have been classified as "molecular chaperones" by Dingwall, C. K. & Laskey, R. A. *Seminars in Cell Biol.* 1, 11–17 (1990), or "polypeptide chain binding proteins" by Rothman, J. E. *Cell* 59, 591–601 (1989), based on their ability to prevent the formation of wrong protein aggregates by binding to unfolded or partially denatured polypeptides. The heat-shock proteins of the hsp70 and hsp60 families are typical representatives of this heterogeneous group of components, as reviewed by Langer, T. & Neupert W. in *Curr. Topics in Microbiol. and Immun.* 167, 3–30 (1991); Pelham, H. R. B. *Nature* 332, 776–777 (1988); and Hartl, F.-U *Seminars in Immunol.* 3, in press (1991).

U.S. Ser. No. 07/261,573 filed Oct. 24, 1988, first described the folding function of hsp60, isolated from yeast mitochondria, and related proteins such as groEL, isolated from *E. coli*. The essential function in protein folding of the members of the hsp60 family has since been demonstrated in vivo and in vitro. These so-called "chaperonin", described by Hemmingsen, S. M., et al., *Nature* 333, 330–334 (1988), include the groEL protein of *E. coli* and other bacteria, reviewed by Georgopoulos, C., et al., *J. Molec. Biol.* 76, 45–60 (1973); Stornborg, N. *J. molec. Biol.* 76, 25 44 (1973); Hendrix, R. W. *J. molec. Biol.* 129, 375–392 (1979); Bochkareva, E. S., et al., *Nature* 336, 254–257 (1988); Goloubinoff, P. et al., *Nature* 342, 884–889 (1989); Van Dyk, T. K., et al., *Nature* 342, 451–453; Lecker, S., et al. *EMBO J.* 8, 2703–2709 (1989); Laminet, A. A., et al., *EMBO J.* 9:2315–2319 (1990); Buchner J., et al. *Biochemistry* 30, 1586–1591 (1991), the rubisco binding-protein of chloroplasts, reviewed by Barraclough, R. & Ellis, R. J. *Biochim. Biophys. Acta* 608, 19–31 (1980); Musgrove, J. E., et al., *Eur. J. Biochem.* 163, 529–534 (1987); and Gatenby, A. A. & Ellis R. J. A. *Rev. Cell Biol.* 6, 125–149 (1990), and the mitochondrial hsp60, reviewed by McMullin, T. W. & Hallbert, R. L. *Molec. Cell. Biol.* 8, 371–380 (1988); Reading, D. S., et al., *Nature* 337–655–659 (1989); Cheng, M. Y., et al. *Nature* 337, 620–625 (1989); Ostermann, J., et al., *Nature* 341, 125–130 (1989); and Cheng, M. Y., et al., *Nature* 348, 455–458 (1990). They form tetradecameric complexes composed of two stacked 7mer rings of approximately 60,000 Dalton subunits that have ATPase activity.

GroEL and the mitochondrial hsp60 functionally cooperate with an additional component, groES, described by Chandrasekhar, G. N., et al., *J. Biol. Chem.* 261, 12414–12419 (1986); Lubben, T. H., et al., *Proc. Natl. Acad. Sci. U.S.A.* 87, 7683–7687 (1990); and Viitanen, P. V. et al. *Biochemistry* 29, 5665–5670 (1990), a ring-shaped complex of seven approximately 10,000 Dalton subunits which has been reported by Chandrasekhar and Viitanen to inhibit the ATPase activity of groEL. The groE proteins are required for lambda phage head-assembly. The rubisco binding-protein mediates the assembly of hexadecameric ribulose bisphosphate carboxylase (rubisco) in chloroplasts. The assembly of dimeric prokaryotic rubisco has been successfully reconstituted in vitro using purified groEL and groES by Goloubinoff, et al., and Viitanen, et al. Recently, the mitochondrial hsp60 has been shown to be necessary not only for the oligomeric assembly of proteins but also for the chain folding of monomeric polypeptides. However, the molecular mechanism of this ATP-driven process remains to be elucidated, and, as a result, how to use and manipulate this mechanism on a practical basis.

It is therefore an object of the present invention to provide all of the components, in purified form, and the method of use thereof, for refolding proteins in vitro, whether synthesized from recombinant sequences or denatured by heat or chemical means.

It is a further object of the present invention to provide the eukaryotic equivalent of groES.

SUMMARY OF THE INVENTION

The mechanisms and components required for chaperon-independent folding of proteins has been elucidated using the groEL and groES proteins of *E. coli* to reconstituted two monomeric enzymes, dihydrofolate reductase (DHFR) and rhodanese. While DHFR is able to fold spontaneously upon dilution from denaturant, this is not observed with rhodanese. Folding reactions were monitored by measuring endogenous tryptophan fluorescence, adsorption of the hydrophobic fluorescent dye anilino-naphthalene-sulfonic acid, protease sensitivity and enzyme activity. The results demonstrate that: i) groEL, or its eukaryotic equivalent hsp60, stabilizes an early intermediate on the folding pathway which appears to be the equivalent to the folding state described as "molten globule"; ii) ATP-dependent folding occurs at the surface of groEL via intermediate conformations which are progressively more compact but still enzymatically inactive; iii) by regulating the groEL ATPase, groES, or its eukaryotic equivalent, accomplishes a critical folding step(s) at groEL by modulating step-wise, ATP-dependent release of the protein substrate from the groEL scaffold.

The essential elements for properly folding any protein are Mg-ATP (provided in the preferred embodiment as 5 mM Mg acetate and 1 mM ATP), groEL or hsp60 14mer, and groES or eukaryotic equivalent. These can be provided in groES purified form or as a semi-purified cell extract. The groES eukaryotic equivalent, encoded by a gene which does not hybridize to the groES gene, can be isolated using the same technique as was described to isolate Hsp60: isolation of a temperature sensitive lethal yeast mutant (petite at permissive temperature) defective in folding and assembly of imported proteolytically processed human ornithine tran-scarbamylase (OTC). The yeast mutant is used to identify a yeast genomic DNA sequence that rescues the mutant following library transformation. The rescuing DNA is isolated, characterized, and expressed. The expressed protein is used to make an antibody which is in turn used to identify the protein in yeast mitochondrial extracts and facilitate biochemical isolation of the protein.

BRIEF DESCRIPTION OF THE DRAWINGS

FIG. 2 are graphs of the groE-dependent reactivation of rhodanese.

FIG. 3 are graphs of the folding of rhodanese at the surface of groEL.

FIG. 4 are graphs showing the ATP-requirement of groE-dependent refolding of rhodanese.

DETAILED DESCRIPTION OF THE INVENTION

GroE-mediated folding of two monomeric enzymes has been reconstituted in vitro. GroEL stabilizes the polypeptides in a molten globule-conformation. GroES and Mg-ATP then promote the acquisition of ordered tertiary structure at the surface of groEL. Folding requires the hydrolysis of approximately 100 ATP molecules per protein monomer, and a solution concentration of at least 1 mM ATP and 5 mM $Mg^{++}$. This active process of surface-mediated chain folding represents a general mechanism for the formation of protein structure in vivo.

For general purposes, the following reagents can be combined to promote proper folding of proteins: Mg-ATP, groEL or Hsp60 14mer, and groES 7mer or eukaryotic equivalent protein. As used herein, the proteins are collectively referred to as the "chaperoning" protein system. These can be obtained or prepared as follows:

Magnesium and ATP

Magnesium is preferably provided as a 5 mM solution of magnesium acetate, either in cell culture fluid or a buffered solution. ATP must be provided in a hydrolyzable form, preferably in a concentration of at least 1 mM ATP.

GroEL and GroEs proteins

GroEL and groES proteins can be purified as described by Lecker, S., et al. *EMBO J.* 8, 2703–2709 (1989) or Viitanen, P. V. et al. *Biochemistry* 29, 5665–5670 (1990), the teachings of which are specifically incorporated herein, using a groE overproducing strain of *E. coli* harboring the plasmid pOF39, described by Fayet, O., et al., *Molec. Gen. Genet.* 202, 35–445 (1986). This strain can be obtained from Costageorgopoulos, at the University of Geneva.

For purification of groEL, the cells are first sonicated at 4° C., debri removed by centrifugation for 5 min×1000 g, then the supernatant placed on a sucrose gradient. The 10 to 30% fraction is centrifuged overnight at 4° C., the 20 S fraction collected and precipitatedd with ammonium sulfate. The 30 to 60% ammonium sulfate fraction is collected, resuspended in buffer, and subjected to DEAE chromatography using a salt gradient equivalent to 50 to 250 mM NaCl. GroEL elutes at 170 mM NaCl. This fraction is then subjected to chromatography on a P100™ column (Pharmacia Fine Chemicals, New Jersey), and the fraction containing groEL subjected to chromatography on a Superose™ 6 (Pharmacia) column. The groEL elutes from this column at near homogeneity.

GroES is isolated from the same overproducing strain of *E. coli*. The cells are sonicated, centrifuged, and the supernatant applied to a sucrose gradient. GroES is found near the top of the gradient, as monitored by gel electrophoresis. The groES fraction is precipitated with ammonium sulfate. The groES is found in the 30 to 60% fraction. This is centrifuged, resuspended, and chromatographed on DEAE chromatography using a 50 to 250 mM NaCl salt gradient. The groES is found in the 120 mM NaCl fraction. This faction is purified to near homogeneity by chromatography first on a Superose 6™ column, then on a Superose 12™ column.

Hsp60 and eukaryotic equivalent of GroES proteins

The hsp60 proteins can be provided in purified form or in the form of a partially purified cell extract (free of whole cells and nuclear materials such as DNA, cellular membrane proteins and lipids). The cell extract is normally a yeast mitochondrial matrix preparation containing hsp60. Mitochondrial matrix preparations are described by Cheng, et al., *Proc. Nat. Acad. Sci. USA* 84:4063–4067 (1987) and McMullin, et al., *Mol. Cell. Biol.* 8:371–380 (1988). Briefly, cells are lysed by sonication, osmotic shock, or a phospholipase, followed by centrifugation in a density gradient to remove membranes and associated proteins, which are solubilized with detergent to release the components of the inner membrane.

Hsp60 can be isolated from yeast cell extracts using an antibody such as the antibody described by McMullin, et al., *Mol. Cell. Biol.* 7:4414–4423 (1987) using known immunoaffinity methodology, or more preferably, expressed from an isolated nucleotide sequence encoding the protein in an appropriate host system. Such a sequence and methods for expression thereof are described in U.S. Ser. No. 07/261,573 filed Oct. 24, 1988, the teachings of which are incorporated herein.

The isolation and identification of the gene encoding Hsp60 from yeast, as described in U.S. Ser. No. 07/261,573 filed Oct. 24, 1988, using a temperature sensitive OTC yeast mutant, can be used to isolate the gene for the eukaryotic equivalent of the groES protein. The following is a description of how the gene encoding hsp 60 was isolated.

Conditional yeast mutants affecting the mitochondrial-import machinery were isolated using a strategy based on the presumption that (1) obstruction of import of essential metabolic enzymes that reside within mitochondria is lethal and (2) when the subunit precursor of the human mitochondrial matrix enzyme ornithine transcarbamylase (OTC) is expressed in yeast, the precursor follows the same pathway of import employed by endogenous yeast mitochondrial precursors.

Temperature-sensitive (ts) lethal mutants were derived from a *Saccharomyces cerevisiae* yeast strain that is defective at the yeast OTC locus (Arg 3) but that contains in its URA 3 locus an integrated segment containing the human OTC coding sequence joined with an inducible yeast Gal 1 promoter (GALOTC strain). Expression of human OTC at non-permissive temperature was induced and production of OTC enzyme activity determined in order to identify temperature shock (ts) mutants affected in mitochondrial import.

A group of mutants that failed to demonstrate activity was isolated. These mutants were further analyzed by immunoblot analysis of extracts with anti-OTC antiserum. Two classes of mutant were distinguished. In one class, precursors of both human OTC and endogenous yeast mitochondrial proteins accumulated at non-permissive temperature. Complementation analysis of this class revealed three groups, called mif 1, 2, and 3 (mitochondrial import function mutants). mif 1 and 2 were shown to encode the two subunits of the mitochondrial processing protease, the processing enhancing protein (PEP) and the matrix processing peptidase (MPP), respectively. In the second class of ts lethal mutants, the mature-size OTC subunit was observed at non-permissive temperature ($M^+$) but no OTC enzyme activity could be detected ($A^-$). Three different molecular defects could explain such a phenotype: (1) A defect in translocation, leaving OTC subunits only partway translocated through the mitochondrial membranes, in a position where they were able to be cleaved by the matrix processing enzyme to a mature size but were not able to be further translocated through the membranes to a position where they could contact each other to assemble into the active homotrimeric enzyme; (2) A defect in the OTC subunit itself, allowing OTC subunits to be completely translocated to the matrix space but blocking their assembly into enzymatically active homotrimer; and (3) A defect in a mitochondrial component that normally plays a role in assembly of subunits reaching the matrix space. The second type of defect would not lead by itself to a lethal phenotype because OTC activity is not required for growth of cells as long as arginine is provided in the growth medium. However the first and third types of defect could produce a lethal phenotype because these defects could involve components likely to play a general role in import.

To determine whether any of the mutants exhibited a defect of either translocation or assembly, each mutant was cured of the human OTC sequence, transformed with a new Gal-OTC segment, and tested at 37° C. for both the size of OTC subunits and the presence of enzyme activity. More specifically, each mutant was first mated with an Arg 3 strain and sporulated. Tetrads were then examined for 2:2 ts lethal behavior to demonstrate that a single lethal mutation was present in the original mutant strain. Spores were also tested for the absence of the URA 3 gene in order to identify ts spores in which the ts mutation had segregated away from the original integrated Gal-OTC-URA 3 segment.

Ts ura$^-$ spores were transformed with a new Gal-OTC-DRA 3 segment. The ura$^+$ transformants were examined for OTC activity after galactose induction at 37° C. Nine out of ten mutants exhibited normal levels of activity, suggesting that they had originally harbored two mutations, one a ts lethal mutation that does not directly affect the import pathway, and a second mutation affecting the human OTC sequence.

One of the ten mutants, alpha-143, also referred to as ts143, behaved differently. As in the other mutants, mature size OTC subunits were detected following induction at 37° C. However, no OTC activity was detected in this mutant. When examined at the permissive temperature, 23° C., this mutant behaved like wild-type. Both mature subunit and OTC activity were detected. It was determined that ts143 contained a single ts lethal mutation that affects the ability of mature-size wild-type human OTC subunits to produce enzyme activity.

To determine whether OTC subunits in the ts143 cells had assembled into homotrimeric enzyme, an assay was carried out using the OTC substrate analogue, delta-N phosphonoacetyl Lornithine (PALO). Total cell extracts were prepared from both ts143 and wild-type cells grown for 2 hours at 37° C. in galactose medium. The extracts were applied to columns containing PALO linked to epoxy-Sepharose™. Column eluents were collected and immunoprecipitated with anti-OTC antiserum. The precipitates were solubilized, fractionated in SDS-PAGE, and the gel immunoblotted with anti-OTC antiserum. When wild-type extracts were applied to the column, no mature size subunit was observed in the flow-through fraction (CE and BK), consistent with the ability of the substrate analogue to quantitatively bind assembled OTC enzyme. In contrast, when an extract of ts143 cells was applied, the flow-through was found to contain both precursor and mature size OTC subunits, in an amount corresponding to that applied.

Both wild-type and ts143 columns were next washed with buffer containing 40 mM KCl (SW). No OTC submits eluted from either column, indicating absence of nonspecific binding. The columns were then washed with the OTC substrate carbamyl phosphate (Cp). An amount of mature-size OTC subunit corresponding approximately to that originally applied eluted from the wild-type column. In the case of the ts143 column, neither OTC precursor nor mature OTC subunit was detected, demonstrating the quantitative passage of subunits through the column during the initial application of extract. These results lead to the conclusion that mature-size wild-type human OTC subunits are produced in ts143 cells at 37° C., but fail to assemble into homotrimeric, catalytically active, OTC enzyme.

To isolate a wild-type copy of the gene affected in ts143, the haploid strain was transformed with a CEN library substantially identical to that of ATCC Deposit No. 37415 prepared using shuttle vector YCp50 (ATCC 37419) described by Rose et al., Gene, 60:237–243 (1987), containing fragments of yeast genomic DNA inserted into a plasmid that contains both a centromere sequence and a URA3 marker. The particular library utilized was a retained library that was obtained directly from Dr. Peter Novick, a co-author of the above Rose et al. article. That library was therefore substantially the same as ATCC No. 37415.

In one strategy of genetic rescue, URA$^+$ transformants were selected at 23° C., then replica plated to rich medium (YPD) at 37° C. In a second strategy, yeast cells were directly plated on YPD medium at 37° C. following transformation.

In both cases, DNA was prepared from colony-purified transformants and used to transform $E.$ $coli$ to ampicillin-resistance. Plasmid DNAs were then isolated and characterized by restriction analysis. Plasmids from the strategy involving initial URA selection at 23° C. followed by replica plating to 37° C. all shared several restriction fragments containing inserted yeast genomic DNA. Plasmids from the strategy involving direct plating at 37° C. exhibited not only this pattern in several isolates but also other distinct restriction patterns each isolated independently more than once.

The rescuing plasmids were then tested to see if they encoded a heat shock protein. Yeast DNA inserts from the plasmids were nick-translated and used to probe blots containing RNA prepared from wild-type yeast grown at 23° C. and either maintained at this temperature or exposed first to an incubation at 42° C. for one hour. The results of this study with the insert from a plasmid designated p8 belonging to the unique group of plasmids obtained by both rescue strategies indicated an increase in the amount of assayed-for RNA in the cells incubated at the higher temperature than those incubated at the lower temperature. Plasmid P8 was determined to contain plasmid YCp50 plus the gene for the rescuing protein, hsp60.

This gene was then isolated and sequenced using standard techniques, as described in U.S. Ser. No. 07/261,573 filed Oct. 24, 1988.

Substantially the same technology has been used to isolate mutants defective in the eukaryotic equivalent of groES. The gene encoding this protein can be isolated using the temperature sensitive lethal yeast mutants (petite at permissive temperature) defective in folding and assembly of imported proteolytic processed human ornithine transcarbamylase (OTC). The yeast mutant is used to identify a yeast genomic DNA sequence that rescues the mutant following library transformation. The rescuing DNA is isolated, characterized, and expressed. The expressed protein is used to make an antibody which is in turn used to identify the protein in yeast mitochondrial extracts and facilitate biochemical isolation of the protein. The encoded protein is expected to have a molecular weight of approximatley 10,000 Daltons and to be encoded by a nucleotide sequence of approximately 300 base pairs.

Folding of proteins using the proteins in combination with Mg-ATP

The purified reagents can either be added to the system in which the protein to be properly folded (either as it is synthesized or after chemical or heat denaturation) is present, or the genes encoding the relevant proteins expressed in the cell culture system in which the protein to be properly folded is being expressed. In the preferred embodiment, the genes for the groE or hsp60 proteins are introduced into the cell culture system using an appropriate vector. Such vectors are commercially available, for example, from BioRad Laboratories, Richmond, Calif. or from International Biotechnologies, Inc., either for expression of proteins in procaryotic or eukaryotic cell culture. The gene to be expressed is inserted into the vector and the cells in which the gene is to be expressed as described by the supplier. Suitable cell culture systems include $E.$ $coli$, yeast such as $S.$ $cerevisae$, and mammalian cells such as CHO cells, all available from a variety of sources, including the American Type Culture Collection of Rockville, Md.

The chaperonin protein system is added to the protein to be folded/refolded under conditions generally in the range of a temperature of between about 1° C. and 40° C., preferably between 15° and 23° C., at a pH of between about 7 and 8.0, preferably at about 7.4. The chaperonin proteins, for example, the groEL 14mer and the groES 7mer, are added in a preferred ratio of 1:1 to the protein substrate, at a ratio of chaperonin proteins to substrate of at least 1:1, preferably at a ratio of 1:3 or 4. The time required for folding is short; i.e., minutes or less for a mature protein, simultaneously with the production of a newly expressed protein.

The method and reagents of the present invention will be further understood by reference to the following non-limiting examples of the refolding of two distinct enzymes using purified groEL and groES in the presence of Mg-ATP. Reconstitution of Chaperonin-Dependent Folding Chicken DHFR is a globular, single-domain protein of 189 residues. Upon dilution from denaturant, DHFR refolds to greater than 90% of the activity of the native enzyme. This property was used to establish the conditions allowing binding of DHFR to purified groEL. These experiments were performed at 15° C. to obtain a better resolution of the time-course of reactivation.

The following methods and reagents were used. The results are shown in FIGS. 1a, 1b, 1c, and 1d.

GroEL and groES proteins were purified to greater than 95% purity using a groE overproducing strain of $E.$ $coli$ harboring the plasmid pOF39, as described above.

Figure 1A:
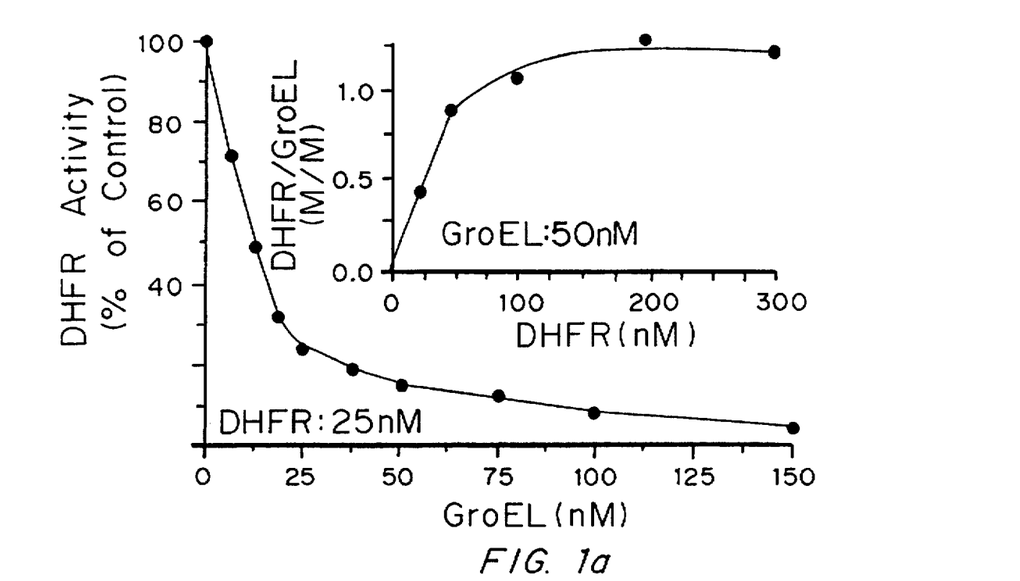
FIG. 1a is a graph of DHFR activity (% of control) versus concentration of groEL (nM)

As shown in FIG. 1a, chicken DHFR (greater than 95% purity, Sigma) was denatured at 100 μg/ml in buffer A (6M guanidinium-HCl (GdmCl), 30 mM Tris pH 7.4, 1 mM dithiothreitol (DTT)) and diluted at 15° C. 200-fold into buffer B (30 mM Tris pH 7.2, 2 mM DTT, 50 mM KCl) containing 50 μM dihydrofolate and purified groEL 14mer as indicated in FIG. 1. Reactivation was measured photometrically by monitoring the oxidation of NADPH at 340 nm. Binding to groEL was analyzed by adding increasing amounts of denatured DHFR at 15° C. to buffer B containing 50 nm groEL; the final concentration of GdmCl was adjusted to 100 nM. After 5 min of incubation, the reactions were separated on 5 ml Sephacryl™ S300-columns (Pharmacia), allowing complete separation between groEL-bound and free DHFR. Fractions (120 μl) containing the peak concentrations of groEL were pooled and analyzed by SDS-polyacrylamide electrophoresis (SDS-PAGE) and immunoblotting using anti-DHFR and anti-groEL antibodies were visualized by the luminescence-based detection system ECL (Amersham). Fluorographs were quantified by laser-densitometry using known amounts of groEL and DHFR as standards.

Figure 1B:
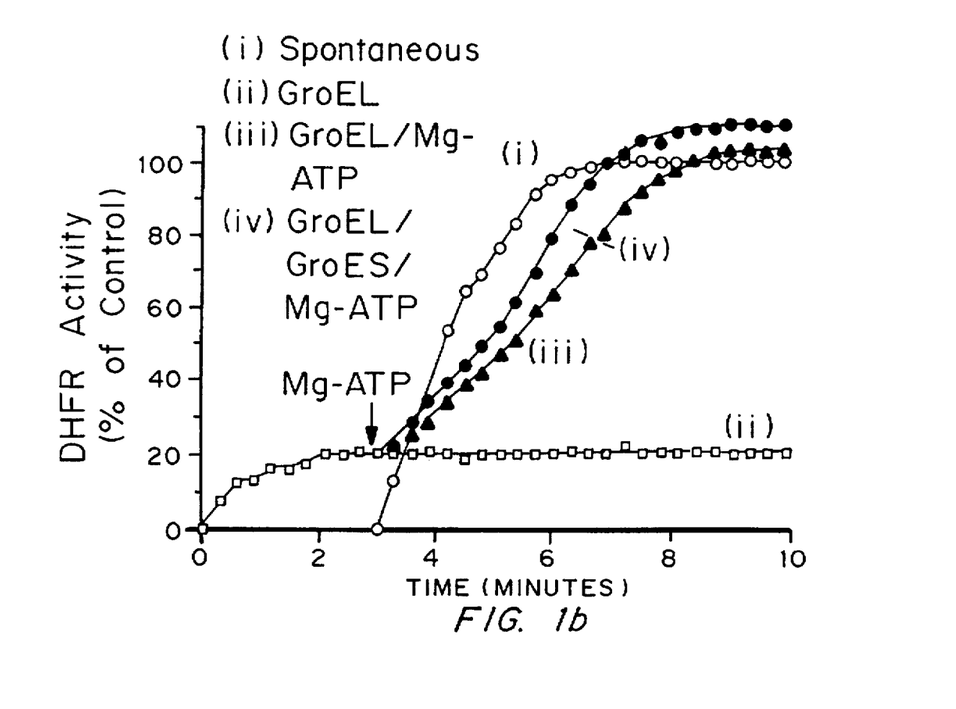
FIG. 1b is a graph of DHFR activity (% of control) versus time in minutes.

As shown in FIG. 1b, unfolded DHFR (25 nM, final concentration) was diluted into buffer B in the absence or presence of 50 nM groEL. Reactivation was started by adding 5 mM Mg-acetate/1 mM ATP after 3 min when spontaneous refolding of free DHFR was complete. When indicated, groES 7mer (50 nM, final concentration) was added prior to MG-ATP. Progress curves of activity were recorded by plotting the changes in absorption at 340 mn ( A/17 sec) versus time.

Figure 1C:
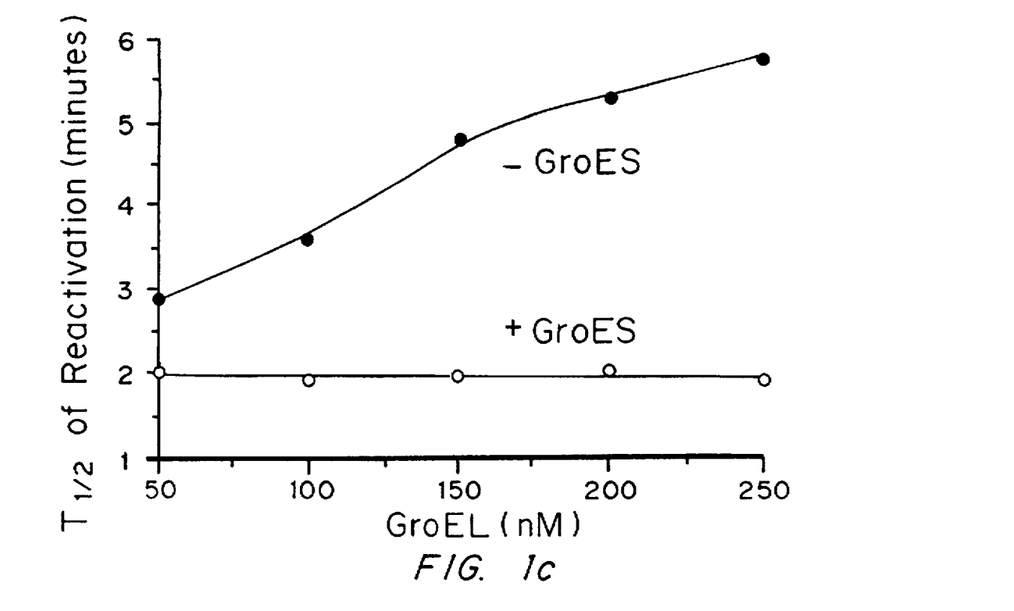
FIG. 1c is a graph of $T_{1/2}$ of reactivation (minutes) versus concentration of groEL (nM) and FIG. 1d is a graph of $T_{1/2}$ of reactivation (minutes) versus concentration of casein (nM), showing groE-dependent reactivation of unfolded DHFR. a, inhibition of spontaneous refolding by increasing concentrations of groEL; Insert, binding of DHFR to groEL; b. time course of reactivation in the absence (1) or presence of groEL (ii–iv), groES (iv) and Mg-ATP (iii, iv). The time point of addition of Mg-ATP is indicated by an arrow; c, influence of increasing concentrations of groEL on $t_K$ of Mg-ATP-dependent reactivation in the presence or absence of groES; d, effect of casein on $t_K$ of MG-ATP-dependent reactivation of DHFR in the presence or absence of groES. The activity of DHFR reached by spontaneous refolding is set to 100%.

As shown in FIG. 1c, the DHFR-groEL complex was generated as in (a) (final concentrations of groEL and DHFR 50 nM and 25 nM, respectively). After 3 min of incubation, increasing amounts of groEL were added in the presence or absence of equimolar amounts of groES. Total concentrations of groEL are indicated. Reactivation was initiated by adding Mg-ATP as above. Based on progress curves, $t_K$ is defined as the time required for 60% reactivation considering that approximately 20% of total DHFR activity was due to spontaneous reactivation.

Figure 1D:
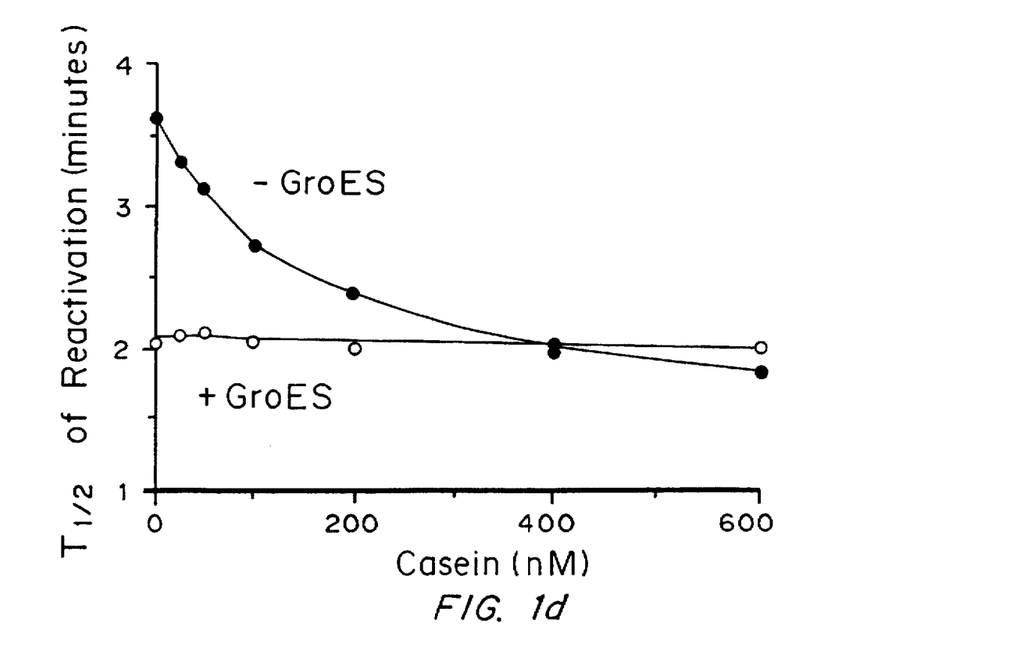

As shown in FIG. 1d, unfolded DHFR (25 nM) was diluted into buffer B containing 100 nM groEL in the presence or absence of groES (100 nM). After 3 min, $\alpha_{s1}$-casein (Sigma) was added at the indicated concentrations. After continuing incubation for 3 min to confirm stability of the DHFR-groEL complex, MG-ATP was added and $t_K$ of reactivation was determined as in (c).

DHFR was completely unfolded in 6M guanidinum-HCl (GdmCl) as based on circular dichroism-spectroscopy and then diluted 200-fold into physiological buffer containing increasing concentrations of groEL (FIG. 1a). An equimolar concentration of groEL (25 nM with respect to groEL 14mer) reduced the yield of reactivated DHFR by about 80%. Unfolded DHFR bound to groEL with high affinity which was not influenced significantly by the present of ATP (in the absence of $Mg^{2+}$) or the non-hydrolyzable ATP analogue AMP-PNP. The groEL 14mer appears to bind only 1–2 molecules of DHFR (FIG. 1a, insert). Addition of Mg-ATP to the DHFR-groEL complex allowed refolding to occur with a half-time of approximately three min (FIG. 1b). This was considerably slower than the spontaneous folding of DHFR ('½ approximately 1 min). In the presence of groEL, reactivation curves were sigmoidal, suggesting the existence of additional species of DHFR during refolding other than the fully unfolded and native forms. GroES 7mer added at a 1:1 molar ratio to groEL accelerated the groEL-dependent folding. Higher amounts of groES were without further effect.

Starting with the preformed DHFR-groEL complex, increasing the concentration of groEL was found to retard the Mg-ATP-dependent reactivation of DHFR (FIG. 1c). This suggested that, following release, DHFR could re-bind to groEL before completing folding. This was demonstrated using $\alpha_{s1}$-casein as a competitor of protein binding to groEL (FIG. 1d). Casein was chosen because it has certain properties of a partially denatured protein. Although being soluble, the native form exposes a considerable part of its hydrophobic residues to solvent and contains a high amount of disordered structure. Casein bound to groEL with high affinity and thereby prevented the re-binding of DHFR to groEL. Displacement of DHFR by casein apparently required ATP-hydrolysis since it was only detected in the presence of Mg-ATP, at least with the concentrations of casein employed. Notably, the decreased rate of reactivation due to the re-binding of DHFR was not observed when groES was present in amounts stoichiometric to groEL (FIG. 1c, d). It thus appears likely that only when groES is absent does DHFR reach its native state via cycles of repeated binding to groEL and Mg-ATP-dependent release.

In contrast to DHFR, a number of proteins do not refold spontaneously upon dilution from denaturant but rather form misfolded aggregates. GroEL and groES allowed the efficient refolding of one such monomeric enzyme, rhodanese of bovine liver. Rhodanese (293 residues) is considerably larger than DHFR and, in contrast to the former, is composed of two equal-sized domains which are stabilized by hydrophobic interactions.

The following methods and materials were used to demonstrate refolding of rhodanese. Rhodanese from bovine liver (greater than 95% purity, Sigma) was denatured in buffer A.

Figure 2A:
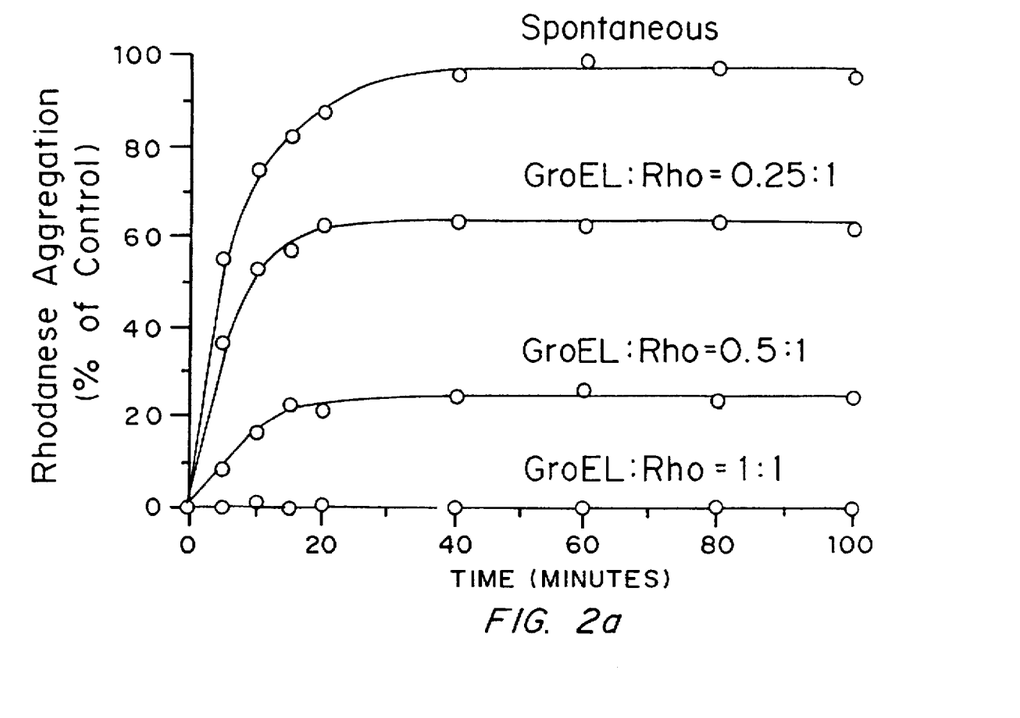
FIG. 2a is a graph of rhodanese aggregation (% of control) versus time (minutes) as a function of groEL to Rhodanese concentration.

As shown in FIG. 2a, unfolded rhodanese was diluted 100-fold (0.46 µM, final concentration) into buffer C (30 mM Tris pH 7.2, 50 mM KCl) containing 0, 0.12, 0.23 and 0.46 µM groEL 14mer, respectively. Aggregation (turbidity) was measured as absorbance at 320 nm.

Figure 2B:
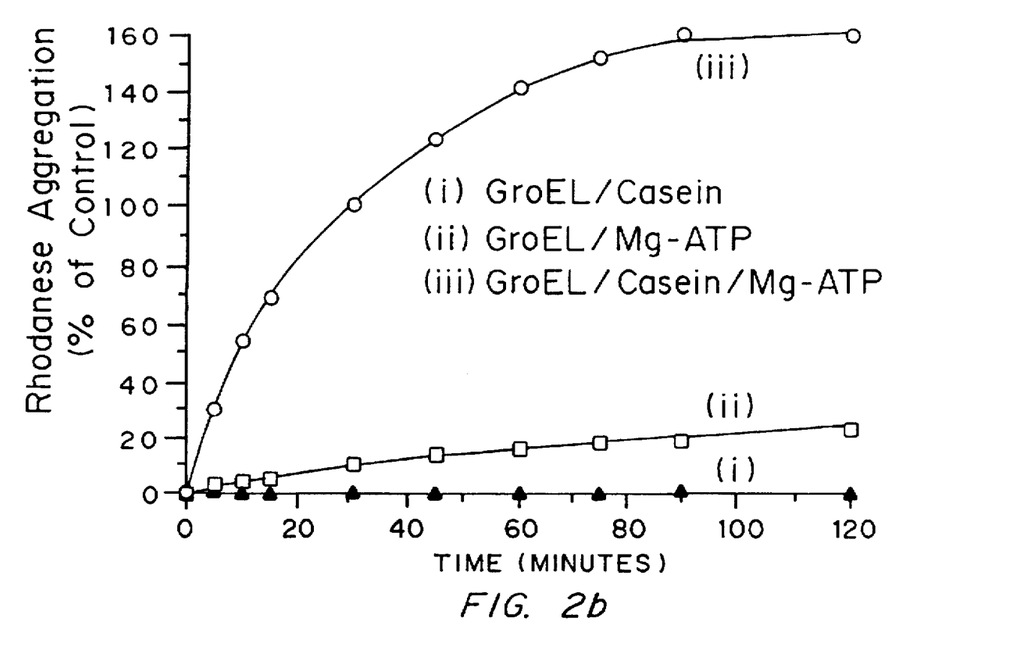
FIG. 2b is a graph of rhodanese aggregation (% of control) versus time (minutes) as a function of the presence of groEL, Mg-ATP, and/or casein.

As shown in FIG. 2b, rhodanese-groEL complex was generated as above (final concentrations of rhodanese and groEL 0.46 µM and 0.69 µM, respectively). Aggregation of rhodanese was measured as in (a) upon addition of 1 mM ATP and 5 mM Mg-acetate in the absence or presence of 4.4 µM casein. Aggregates were sedimented in an Eppendorf centrifuge while groEL remained in the supernatant fraction.

Figure 2C:
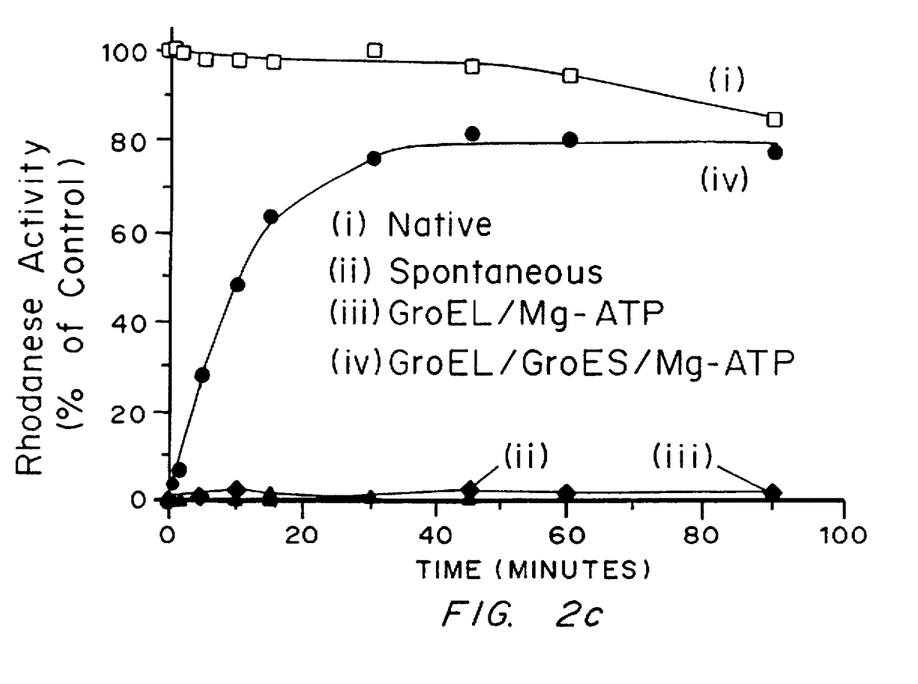
FIG. 2c is a graph of rhodanese (% of control) versus time (minutes) for native rhodanese, spontaneously refolded rhodanese, rhodanese in the presence of groEL/Mg-ATP, and in the presence of groEL/groES/Mg-ATP, showing in a, suppression of rhodanese aggregation by groEL; in b, displacement of rhodanese from groEL by casein (i, iii) in the presence of Mg-ATP (ii, iii). Spontaneous aggregation in the absence of groEL is set to 100%; in c, reactivation of unfolded rhodanese in the absence (i) and in the presence of groEL/Mg-ATP (ii, iii) and groES (iii). The activity of the native rhodanese (iv) is taken as 100%).

As shown in FIG. 2c, rhodanese-groEL complex was formed as in (b). When indicated, groES was present at 0.69 µM. At various times after adding Mg-ATP, enzyme activity was determined (0.14 µM rhodanese, final concentration) in the presence of 10 mM trans-1,2-cyclohexanediaminetetraacetic acid (CDTA) to stop groE-dependent reactivation.

As expected, dilution of rhodanese from 6M GdmCl resulted in extensive aggregation (FIG. 2a). GroEL prevented this aggregation and formed a stable complex with rhodanese. Unlike DHFR, only a small amount of rhodanese was released from groEL upon ATP-hydrolysis; this portion of rhodanese did not reactivate but formed inactive aggregates (FIG. 2b). Complete release of rhodanese was achieved by the competitor casein. Again, this displacement was only observed in the presence of Mg-ATP and, in contrast to the findings with DHFR, resulted in the aggregation of the released protein. Only in the presence of groEs does efficient reactivation of rhodanese ($t^K$~10 min) occur (FIG. 2c), suggesting a specific function of groES for folding beyond just promoting the release of a groEL-stabilized intermediate.

GroEL stabilizes a molten globule-like state

The endogenous tryptophan fluorescence of groEL-bound DHFR and rhodanese was determined as a measure of tertiary structure. GroEL and groES themselves interfere only minimally with this analysis since both components are devoid of Trp residues.

The conformations of groEL-associated proteins were compared by Trp fluorescence of DHFR: (1). in 6M GdmCl; (2). native; (3). groEL-bound DHFR-11; (4). groEL-bound DHFR-12; (5) DHFR-12 after incubation in the presence of DCTA; (6). DHFR after complete reactivation in the presence of groEL and Mg-ATP. (ii). Trp fluorescence of rhodanese: (1). in 6M GdmCl; (2). native; (3). groEL-bound RHO-11; (4). RHO-11 upon incubation with Mg-ATP in the absence of groES; (5). RHO-11 after reactivation in the presence of groES and Mg-ATP; by 1,8 ANS fluorescence of free and groEL-bound forms of DHFR and rhodanese, and of groEL; and by proteinase K resistance of DHFR and rhodanese: (i, iv). native; (ii, v). DHFR-11 and RHO-11, respectively; (iii, vi). DHFR-12 and RHO-12, respectively.

The following materials and methods were used. Fluorescence spectra were recorded on a SPEX spectrofluorimeter. Absorbance of the samples was lower than 0.05 at the excitation wavelength. The substrate-groEL complexes were formed as described above at a 2.5-fold molar excess of groEL 14mer over substrate protein (final concentrations of DHFR and rhodanese, 0.65 µM, respectively). Under these conditions, greater than 90% of DHFR and greater than 95% of rhodanese were bound to groEL. Where indicated, groES 7mer was added at an equimolar concentration to groEL. Trp fluorescence was excited at 295 nm. Spectra were obtained by subtracting the background fluorescence of the respective chemically identical reactions from which DHFR or rhodanese were omitted. Background fluorescence of groEL and groES due to minor impurities was 15–30% of the total fluorescence measured in the presence of substrate proteins. The small amount of DHFR which had escaped binding to groEL was corrected for. Analysis of DHFR-12 in reaction (i) 4 was generated by adding Mg-ATP (1 mM Mg-acetate, 2 mM ATP) to groEL-bound DHFR-11. (Neither ATP nor $Mg^{2+}$ affected the fluorescence properties of DHFR-11) Spectrum (i) 4 was recorded 30 sec and spectrum (i) 6 10 min after addition of Mg-ATP. Unfolding of DHFR-12 (i) 5 was observed upon incubation of reaction (i) 4 in the presence of 10 mM CDTA for 5 min. In reaction (ii) 4, groEL-bound RHO-11 was incubated with Mg-ATP for 30 min. Reactivated rhodanese was analyzed after 40 min incubation of RHO-11 in the presence of groES and Mg-ATP.

Various forms of DHFR and rhodanese prepared as above were incubated for 5 min at 15° C. or 20° C. in the presence of a 20-fold molar excess of 1-anilino-naphthalene-8-sulfonic acid (ANS) for ANS analysis. (GroEL-substrate complexes were stable in the presence of ANS for at least 30 min.) Excitation was at 390 nm and emission was monitored at 470 nm. Emission spectra were corrected for background fluorescence caused by ANS in the presence or absence of groEL. DHFR-12 and reactivated DHFR were formed as above in the presence of ANS and the loss of fluorescence at 470 nm was followed. RHO-12 was generated in the presence of ANS by incubation of RHO-11 with Mg-ATP and groES for 3 min at 25° C. Fluorescence intensity was calculated in arbitrary units per mole of protein (for the 14mer in case of groEL).

GroEL-bound DHFR-11 and DHFR-12 were separated from free DHFR by sizing chromatography as in FIG. 1. GroEL-bound rhodanese was isolated by sedimenting aggregates for 30 min at 25.000 xg. RHO-12 was generated as above (but in the absence of ANS). The reaction was stopped by the addition of 10 mM CDTA and cooling to 0° C. Protease treatment was performed in buffer B (final concentration of DHFR and rhodanese approximately 0.25 µM and 0.95 µM, respectively) for 10 min at 0° C. at concentrations of proteinase K (PK) of 0, 0.5, 1, 5, 10, and 20 µg/ml. Protease action was stopped by adding phenylmethylsulfonylfluoride (PMSF) to 2 mM. TCA precipitates were analyzed by SDS-PAGE and immunoblotting. Fluorographs were exposed for either 15 sec or 90 sec.

DHFR from chicken contains three tryptophans, at positions 24, 57 and 113. Their fluorescence upon excitation at 295 nm changes markedly when the protein is unfolded: the emission maximum (lambda max. em) shifts from 331 nm to 356 nm accompanied by an approximately 2-fold increase in the fluorescence intensity. The red shift of fluorescence generally reflects transfer of Trp residues to a more polar environment. The increase in fluorescence intensity upon unfolding has been shown to be largely due to the removal of quenching amino acids from the neighborhood of the active site residue trp 24. The fluorescence spectrum of DHFR was stabilized by groEL in the absence of ATP-hydrolysis (termed DHFR-11). The lambda max. em was at 345 nm, half-way between the lambda max. em values of the native and unfolded proteins (Table 1). Strikingly, the relative fluorescence intensity of DHFR-11 was almost as high as that of the completely unfolded protein. Apparently, groEL-bound DHFR lacks an ordered tertiary structure. This is consistent with the very high protease sensitivity of the protein. As indicated by the 50% blue shift of emission, the Trp residues in DHFR-11 are already in a more hydrophobic environment relative to the completely unfolded protein. Using acrylamide as quencher, their accessibility to solvent was found to be significantly increased as compared to the native structure. Acrylamide is a polar but non-ionic collisional quencher that may be expected to partition into the loosely-folded interior of folding intermediates.

The properties of groEL-bound rhodanese (RHO-11) were similar to that of DHFR-11. Rhodanese contains eight tryptophans which are distributed throughout the sequence. Upon complete unfolding, their fluorescence maximum shifts from 330 nm to 355 nm without major change in intensity. The lambda max. em of RHO-11 was at 342 nm, again corresponding to an approximately 50% shift towards the unfolded form. The fluorescence intensity of RHO-11 was increased and was characterized by the presence of partially accessible Trp residues. Like DHFR-11, groEL-bound rhodanese exhibited very high protease-sensitivity.

DHFR-11 and RHO-11 were tested to determine if they contained hydrophobic regions that could be detected by 1-anilino-naphthalene-8-sulfonic acid (ANS), a probe for apolar binding sites whose fluorescence is strongly dependent on the hydrophobicity of the environment. ANS is known to accumulate within the solvated hydrophobic core of early folding intermediates generally termed "molten globule" or "compact intermediate".

Table 1 shows the florescence parameters of DHFR and rhodanese species. Trp fluorescence spectra were recorded as described above. Fluorescence quenching using acrylamide (0–400 mM) was measured at the maximum of emission. Quenching data were analyzed according to the Storn Volmer relationship $Fo/F=1+K_Q|X|$, where Fo and F are the fluorescence intensities in the absence and presence of the quencher, respectively, and $|X|$ is the quencher concentration. $K_Q$ is the apparent quenching constant. In the case of heterogeneous emission (i.e. presence of more than one population of Trp residues with different microenvironments) a modified Stern-Volmer equation was applied which allows the calculation of the effective quenching constant. $(K_Q)$eff and the fraction of Trp residues $(f_a)$eff with the highest accessibility to the quencher. Quenching data were corrected for background fluorescence caused by minor impurities of the groEL preparation. The inner-filter effect due to acrylamide was corrected for by the factor Y=antilog $(d_4+d_e)/2$, where $d_4$ and $d_e$ are the absorbances at the excitation and emission wavelengths, respectively. F örster-distances r were calculated on the basis of singlet—singlet energy transfer from Trp residues to 1,8 ANS. Both groEL-stabilized proteins showed strong ANS fluorescence.

TABLE 1

Fluorescence data for groEL-stabilized proteins:

| | Maximum of Tryptophan Fluorescence [nm] | Fluorescence at Emission Maximum [Arb. Units] | $K_Q$ [M] | $f_a$ | r (Trp, ANS) [Å] |
|---|---|---|---|---|---|
| DHFR | | | | | |
| Native | 331 | 6.7 | 2.5 | 1.0 | — |
| 6M GdmCl | 356 | 15.5 | 8.5 | 1.0 | — |
| GroEL-bound (DHFR-11) | 345 | 14.1 | 5.5 | 0.8 | 2.9 |
| Rhodanese | | | | | |
| Native | 333 | 13.1 | 1.5 | 1.0 | — |
| 6M GdmCl | 356 | 12.2 | 9.0 | 1.0 | — |
| GroEL-bound (RHO-11) | 342 | 17.8 | 4.1 | 1.0 | 3.0 |

Notably, the interaction with ANS did not affect the stability of the complex between groEL and the substrate proteins. Little fluorescence was measurable with the native or guanidine-unfolded DHFR and rhodanese, or with groEL 14mer alone, indicating that groEL does not expose domains that could provide a hydrophobic environment for ANS. This does not exclude that groEL may shield hydrophobic regions of the associated proteins, thereby increasing the hydrophobic space accessible to ANS. The near spatial relationship of the tryptophan and ANS chromophores in DHFR-11 and RHO-11 is reflected in fluorescence energy transfer from the Trp residues (excitation at 295 nm) to ANS occurring with an efficiency of approximately 30% (Table 1). The Förster-distances between tryptophans and ANS were calculated as a relative parameter. In both cases a mean distance of approximately 30 Å was found, further suggesting a similar global shape of the two groEL-bound intermediates.

Altogether, these results indicate that groEL stabilizes unfolded substrate proteins in a loose conformation devoid of ordered tertiary structure. The fluorescence properties and the increased solvent accessibility of the Trp residues, as well as the incorporation of ANS, point to the presence of flexible tertiary structure internalizing a fluctuating, hydrophobic core, as described for the molten globule state.

Folding of DHFR Via a More Compact Intermediate

The changes in Trp fluorescence during groEL-dependent folding of DHFR-11 were monitored. Within 15–30 sec of the addition of Mg-ATP to the DHFR-groEL complex, the relative fluorescence intensity of DHFR-11 dropped markedly, approaching that of the native protein, while lambda max, em remained unaltered, defining the folding intermediate DHFR-12. In a subsequent phase extending over 3–7 min. Lambda max, em shifted from 345 nm to 331 nm accompanied by the appearance of enzyme activity. Apparently, a partial folding reaction including Trp 24 occurs early in groEL-dependent folding of DHFR, exposing this residue to the native-like fluorescence quenching environment.

In parallel with the loss of Trp fluorescence, the conformational change to DHFR-12 resulted in a loss of 60% of the ANS fluorescence detected with DHFR-11. This phenomenon is typically observed with certain early folding intermediates, resembling the molten globule, upon their folding to a more compact structure. This could be confirmed by analyzing the endogenous resistance of DHFR-12 towards protease. DHFR-12 was generated by initiating ATP-hydrolysis as above. After 30 sec at 15° C., the folding reaction was stopped by adding the $Mg^{2+}$-chelator CDTA and cooling to 0° C. DHFR-12, in contrast to DHFR-11, was resistant to intermediate concentrations of proteinase K. A small amount of an approximately 10,000 Dalton fragment was detectable which was digested at higher concentrations of protease. In contrast to the protease-stable, native enzyme, DHFR-12 was still associated with groEL. When the reaction containing DHFR-12 and CDTA was maintained at 15° C. (instead of 0° C.), partial unfolding, as visualized by an increase in fluorescence intensity, was observed. Addition of sufficient $Mg^{2+}$ to compensate for the CDTA present re-initiated the folding reaction, leading to the conclusion that the folding of groEL-bound DHFR-11 involves the transient formation of an intermediate with partially native tertiary structure, DHFR-12. This compactization occurs in close association with the groEL complex.

GroES Commits Proteins to Folding at the GroEL Surface

The interaction of groES with groEL was found to accelerate the conversion of DHFR-11 (FIG. 1b) to the native protein, perhaps simply by facilitating its Mg-ATP-dependent release. On the other hand, based on the observation that folding of rhodanese is essentially groES-dependent (FIG. 2c), one would predict that the action of groES allows a critical folding step(s) to proceed at the groEL surface. To test this hypothesis, rhodanese folding was dissected into intermediate steps.

Figure 3A:
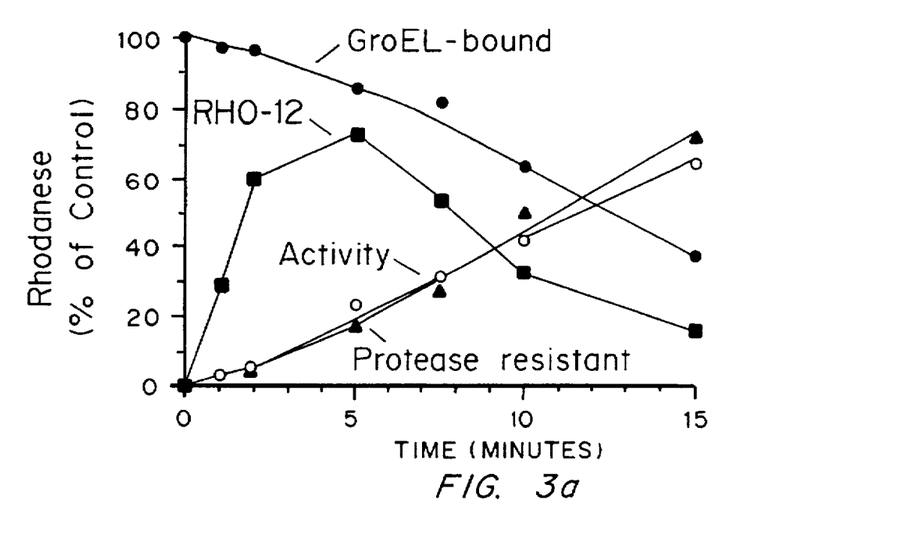
FIG. 3a, graphing rhodanese (% of control) versus time (minutes), shows the time-course of accumulation of groEL-associated RHO-12 and of native rhodanese. The total amount of rhodanese analyzed is set to 100%.

The following materials and methods were used. The results are shown in FIG. 3a for unfolded rhodanese diluted as above from 6M GdmCl into buffer C containing 2.34 μM groEL 14mer. The final concentration of rhodanese was 1.17 μM. After centrifugation to exclude the presence of aggregated rhodanese, 2.34 μM groES was added to the supernatant fraction and refolding was started at 25° C. by addition of ATP and Mg-acetate to 1 and 2 mM, respectively. At the times indicated, folding was stopped in aliquots of the reaction by adding CDTA to 10 mM and cooling to 0° C. Enzyme activity and endogenous protease resistance of rhodanese were determined as in FIG. 2. Rho-11 was defined as the amount of rhodanese resistant to 2 μg/ml proteinase K as quantified by densitometry of fluorographs.

Figure 3B:
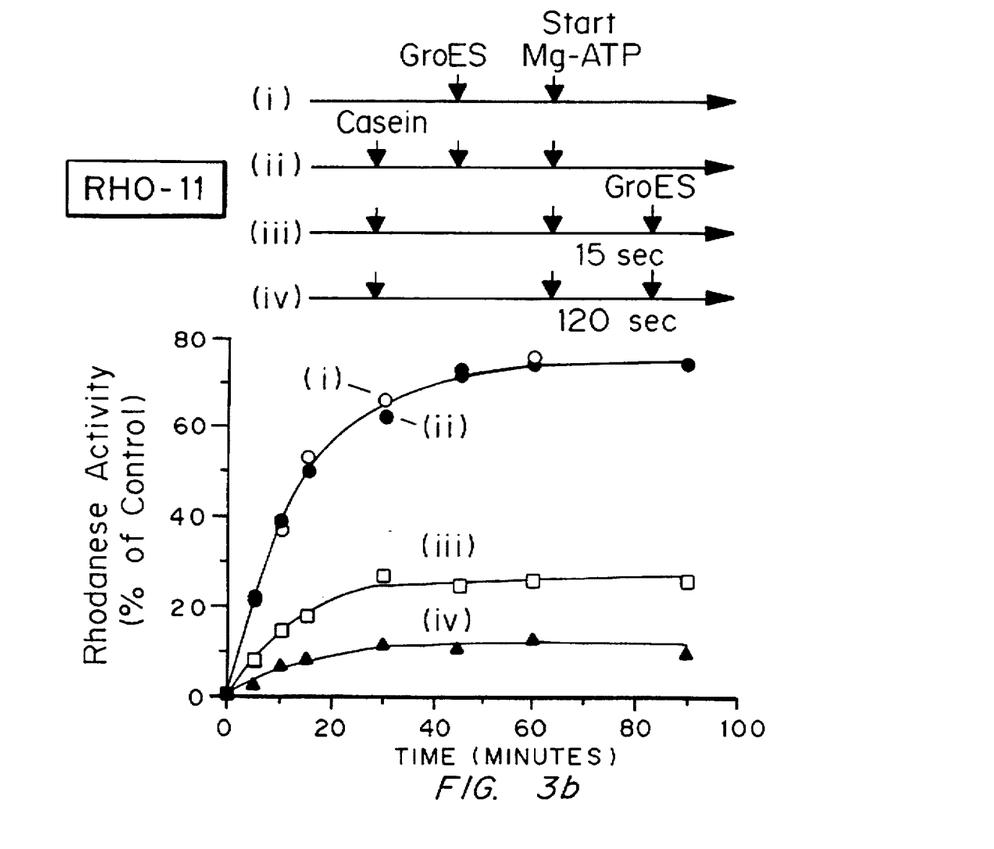
FIG. 3b, graphing rhodanese activity (% of control) versus time (min), shows the reactivation of rhodanese in the absence (i) or presence (ii–iv) of casein adding groES prior to Mg-ATP (ii), and 15 sec (iii) or 120 sec (iv) after starting the reactions with Mg-ATP.

Association with groEL was determined and the results shown in FIG. 3b. Rhodanese-groEL complex (0.46 μM/0.69 μM, respectively) was formed as above. Refolding reactions received 4.4 μM casein, 0.69 μM groES, 1 mM ATP and 5 mM Mg-acetate according to the order of addition indicated.

In the absence of groES, the addition of Mg-ATP had no effect on the fluorescence properties or the protease-sensitivity of groEL-bound RHO-11. The folding reaction in the presence of groES was stopped after various times by adding CDTA to inhibit ATP hydrolysis. The amount of groEL-bound rhodanese, its endogenous protease resistance, and enzyme activity were analyzed during the time-course of the reaction, as shown in FIG. 3a. During the first 5 min of incubation in the presence of Mg-ATP, a form of rhodanese accumulated, defined as RHO-12, which had lost 50% of the ANS fluorescence of RHO-11 and had acquired an increased resistance to intermediate concentrations of proteinase K. The formation of this enzymatically inactive intermediate preceded that of the protease-resistant, active rhodanese which showed only little ANS fluorescence. In contrast to the native enzyme, RHO-12 was still bound to groEL as revealed by gel chromatography (FIG. 3a). Altogether, RHO-12 has properties resembling DHFR-12 but, in contrast to DHFR-12, its formation is critically dependent on groES.

Competition by casein for the groES-dependent conversion to RHO-12 and to the native enzyme would be expected if folding involved cycles of complete release and rebinding to groEL. As shown in FIG. 2b, a 6-fold molar excess of casein over groEL efficiently displaced RHO-11 in the presence of Mg-ATP, resulting in aggregation. When added prior to rhodanese, this amount of casein was sufficient to almost completely prevent the reactivation of rhodanese by groEL and groES. Strikingly, when both casein and groES were added to preformed rhodanese-groEL complex before initiating folding by Mg-ATP, reactivation was as efficient as in the absence of casein (FIG. 3b). Thus, the competitor was unable to interrupt the reactivation once the groEL-rhodanese complex had been formed and groES was present. This indicates that a single round of interaction between rhodanese and groEL is sufficient for folding. On the other hand, when groES was added to a reaction containing rhodanese-groEL complex and casein 15–120 sec after starting ATP hydrolysis, the yield of active enzyme was decreased by 50–80% (FIG. 3c). This corresponded to the amount of rhodanese displaced from groEL during that incubation (see FIG. 2). This lead to the conclusion that during folding to RHO-12, rhodanese maintains contact with the groEL 14mer. In the presence of groES, the protein is committed for folding. The underlying mechanism of this surface-mediated reaction could be a progressive, Mg-ATP-dependent release of the folding polypeptide. Achievement of the native conformation appears to be closely coupled with final release from groEL.

ATP Requirement of Folding

The following materials and methods were used to determine the ATP requirement for folding.

Figure 4A:
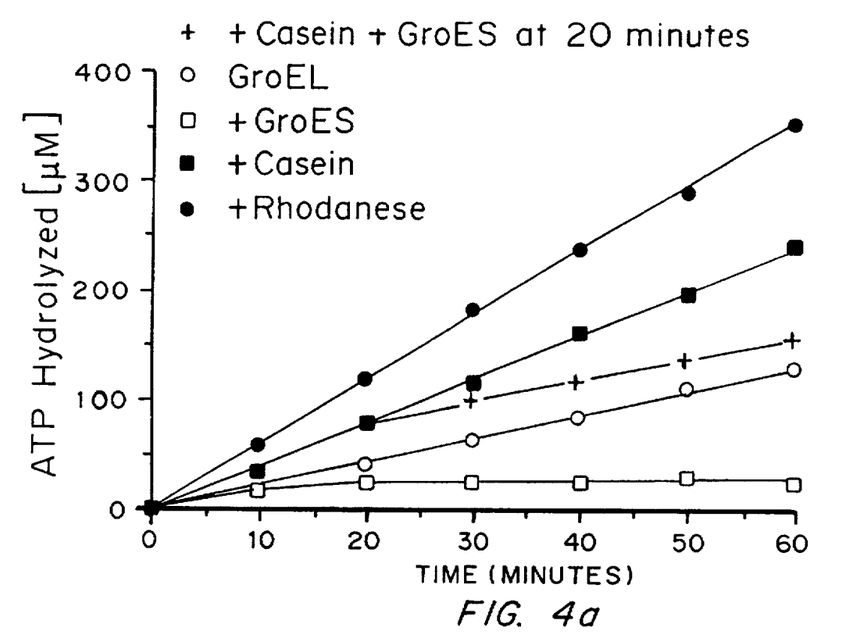
FIG. 4a, graphing ATP hydrolyzed (µM) versus time (minutes), demonstrates the influence of casein, rhodanese and groES on the ATPase activity of groEL.

ATPase-activity was measured at 25° C. by colorimetric determination of free phosphate produced by ATP-hydrolysis using malachite green as color reagent. Spontaneous hydrolysis of ATP as well as free phosphate in reagents were corrected for. One unit of absorbance at 640 nm corresponded to 9.45 nmole phosphate. As shown in FIG. 4a, after addition of groEL (0.33 µM in buffer C) of groES (0.33 µM), casein (4.4 µM) or denatured rhodanese (1.0 µM), ATP-hydrolysis was started with 1 mM ATP and 5 mM Mg-acetate. GroES was added to the reaction containing casein after 20 min of incubation. The final concentration of GdmCl in the assay of greater than 30 mM did not detectably affect the groEL ATPase. Spontaneously aggregated rhodanese (up to 1.6 µM final concentration) did not stimulate the ATPase activity of groEL.

Figure 4B:
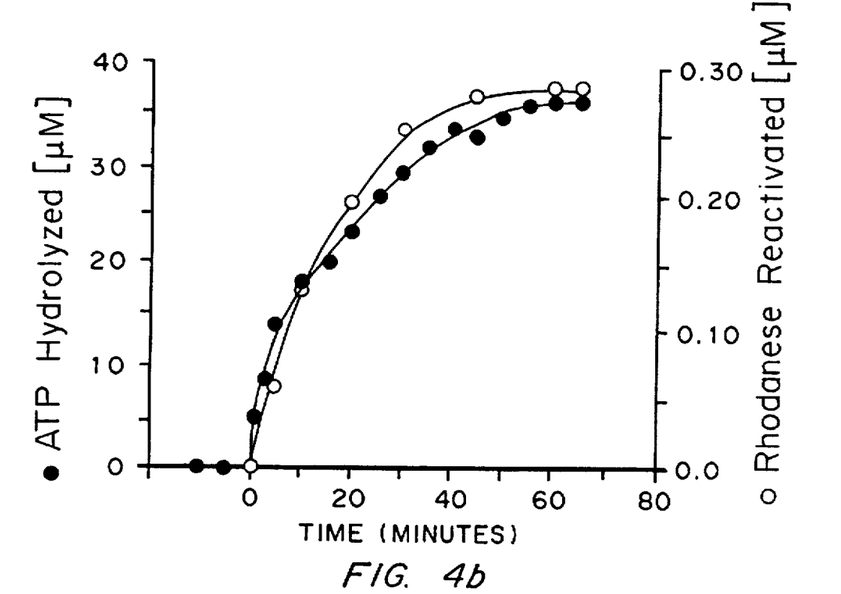
FIG. 4b, graphing ATP hydrolyzed (µM) versus time (min), demonstrates the stoichiometry of ATP-hydrolysis and rhodanese reactivation in the presence of groEL and groES.

As shown in FIG. 4b, GroEL (0.33 µM) and groES (0.66 µM) were preincubated for 30 min at 25° C. in the presence of Mg-ATP to ensure maximal inhibition of the groEL ATPase. Denatured rhodanese was then added to a final concentration of 1.0 µM (t=0 min). Enzyme activity and ATP-hydrolysis were measured in parallel aliquots of the same reaction. The concentration of reactivated rhodanese was calculated based on the specific activity of the native enzyme. (One out of five experiments is shown.)

The ATPase activity of groEL, measurable in the absence of protein substrate, is known to be inhibited by groES. Under the assay conditions described herein, groEL 14mer hydrolyzed ATP at a rate of approximately 7 min$^{-1}$, as shown in FIG. 4a. GroES 7mer, at a 1:1 molar ratio to groEL 14mer, reduced this rate to approximately 0.25 min$^{-1}$ within 5–10 min of addition. Increasing the concentration of groES did not further reduce the rate of ATP-hydrolysis. A saturating concentration of casein caused a 2-fold activation of the groEL ATPase in the absence of groES (FIG. 4a). Binding of unfolded rhodanese also resulted in a continuous stimulation to a rate of approximately 17 ATP hydrolyzed per min. This is consistent with the finding that, in the absence of groEs, the substrate protein and groEL undergo cycles of complete, Mg-ATP-dependent release and re-binding without folding. Under these conditions, the competitor casein will displace 50% of bound rhodanese from groEL within 15 sec of initiation of ATP hydrolysis (FIG. 4b). It is estimated that approximately 27 molecules of ATP are hydrolyzed per molecule of rhodanese released in the absence of groES.

Addition of unfolded rhodanese to groEL and groES initially resulted in an approximately 40-fold increase of the groES-suppressed rate of ATP-hydrolysis (FIG. 4b). The ATPase activity then gradually decreased as reactivation of rhodanese approached completion. It was calculated that 100±20 moles of ATP were hydrolyzed per mole of rhodanese folded (FIG. 4b). Due to the faster kinetics of reactivation, DHFR showed a 2 to 3-fold lower hydrolysis of ATP during groE-dependent folding. In contrast, casein caused a continuous stimulation of the groEL ATPase even in the presence of groES (FIG. 4A). The "native" protein casein appears to be unable to vary structural elements interacting with groEL.

In summary, these results lead to the conclusion that groES couples the groEL ATPase with the folding reaction at the surface of the chaperonin, and that GroES coordinates Mg-ATP-dependent conformational changes of GroEL and thereby allows correct folding to occur by a process of step-wise release. GroES prevents the "whole-sale" dissociation of the substrate protein from groEL which is unproductive for folding.

The conformation of groEL-bound polypeptides resembles that of the so-called "molten globule" or "compact intermediate", a transient, early folding state that rapidly interconverts with the fully unfolded form. It is characterized by containing all or part of the secondary structure of the protein in conjunction with a relatively compact but unordered, flexible tertiary structure internalizing a "molten", hydrophobic core. The groEL-stabilized intermediates, DHFR-11 and RHO-11, fulfill these criteria: i) compared to the fully unfolded state, their tryptophans are in a less polar environment and are only partially exposed; ii) their hydrophobic interior is much less densely packed than that of the native conformation as demonstrated by its solvent accessibility and the typical incorporation of the hydrophobic fluorescent probe ANS; and (iii) their structural flexibility is reflected in the high sensitivity towards protease.

Substrate proteins acquire a more rigid structure while maintaining the interaction with the groEL scaffold. The decrease in fluorescence intensity during conversion of DHFR-11 to DHFR-12 is likely due to the formation of the natural, hydrophobic environment of Trp 24. This is based on findings with a mutant form of human HDHFR in which Trp 24 is changed to Phe; the mutant protein does not show the increase in Trp fluorescence intensity typically observed upon unfolding. DHFR12 and RHO-12 represent more compact conformations on the folding pathway. Apparently, their hydrophobic interior is already more densely packed than in the molten globule-state, explaining the reduced accessibility for the fluorescent probe ANS. The native state of the protein is reached during or shortly after the final release from groEL.

The large groEL 14mer appears to interact with only 1 to 2 substrate molecules. Folding occurs as an active process at the interacting surface between groEL and the substrate protein, relying initially on binding of two (or more) segments of the protein substrate and releasing them sequentially upon ATP hydrolysis. This latter step requires the action of groES, which couples the hydrolysis of ATP with folding at groEL, coordinating the function of (adjacent) parts of the substrate binding-region, belonging to different subunits of groEL, for example, by modulating the time-span during which they are refractory for rebinding to segments of the folding protein. This prevents the release of the complete protein in a single step, and gives a (sub) domain sufficient time to organize to a more compact structure which is no longer able to re-bind. Rhodanese folding is fully dependent on such a mechanism while DHFR, at least in vitro, is not. Nevertheless, the observations made with DHFR are consistent with the above considerations: In the absence of groES, folding is retarded by increasing the concentration of groEL as a result of cycles of unproductive binding and release. This is not the case in the presence of groES, however, apparently because the protein is then forced onto a folding pathway that involves a staged release during a single round of interaction.

The amount of ATP hydrolyzed by groEL per protein molecule folded is in the range of 5 to 10% of the total required for synthesis, suggesting that the structural organization of a polypeptide at the surface of groEL requires multiple rounds of ATP hydrolysis by the groEL 14mer. The energy of the ATP hydrolyzed is not conserved in the final folded structure but is probably required to promote conformational changes of groEL resulting in (sequential) release of the bound substrate. The chaperonins are essential for folding in vivo, i.e., they "catalyze" protein folding in a biological sense.

Modifications and variations of the compositions and methods of use thereof to fold or refold proteins will be obvious to those skilled in the art from the foregoing detailed description. Such modifications and variations are intended to come within the scope of the appended claims.

We claim:

1. A method for folding or refolding proteins in a cell free solution or in cells comprising providing in combination with the protein to be folded a chaperonin protein system comprising isolated groEL or hsp60 14mer, in a ratio of approximately 1:1 to the protein, and $Mg^{++}$-ATP, at a pH of between 7.0 to 8.0 and a temperature of between 1° C. and 40° C., wherein the chaperonin system is provided at a ratio of at least 1:1 chaperonin system to protein to be folded, the magnesium is present in solution at a concentration of at least 5 mM and the ATP is present in solution at a concentration of at least 1 mM or the magnesium and ATP are present in the concentrations normally present in the cells.

2. The method of claim 1 wherein the pH is approximately 7.4 and the temperature is between 15° to 23° C.

3. The method of claim 1 wherein the protein is folded to have increased resistance to proteolytic attack.

4. A method for folding or refolding proteins in a cell free solution or in cells comprising providing in combination with the protein to be folded a chaperonin protein system consisting of isolated groEL or hsp60 14mer, groES 7mer or the eukaryotic protein equivalent, in a ratio of approximately 1:1, and $Mg^{++}$-ATP, at a pH of between 7.0 to 8.0 and a temperature of between 1° C. and 40° C., wherein the magnesium is present in solution at a concentration of at least 5 mM and the ATP is present in solution at a concentration of at least 1 mM or the magnesium and ATP are present at the concentrations normally present in the cells, wherein the protein is folded as it is being synthesized.

5. The method of claim 1 wherein the protein is refolded after being denatured.

6. The method of claim 4 wherein the ratio of groEL 14mer to groES 7mer to substrate protein is at least 1:1.

7. The method of claim 4 wherein the chaperonin folding system is a cell extract.

8. The method of claim 4 wherein the chaperonin folding system comprises purified groEL and groES.

9. The method of claim 1 wherein the chaperonin folding system comprises a mitochondrial matrix extract.

* * * * *